US00RE45963E

(19) United States
(12) Reissued Patent
Heffernan

(10) Patent Number: US RE45,963 E
(45) Date of Reissued Patent: Apr. 5, 2016

(54) SELF-SEALING INFLATABLE ARTICLE

(71) Applicant: Stephen Thomas Heffernan, Arundel (AU)

(72) Inventor: Stephen Thomas Heffernan, Arundel (AU)

(21) Appl. No.: 14/204,809

(22) Filed: Mar. 11, 2014

Related U.S. Patent Documents

Reissue of:
(64) Patent No.: 8,349,417
Issued: Jan. 8, 2013
Appl. No.: 12/738,140
PCT Filed: Nov. 21, 2008
PCT No.: PCT/AU2008/001725
§ 371 (c)(1),
(2) Date: Apr. 15, 2010
PCT Pub. No.: WO2009/065177
PCT Pub. Date: May 28, 2009

(30) Foreign Application Priority Data

Nov. 22, 2007 (AU) ..... 2007906391
Jan. 3, 2008 (AU) ..... 2008900021

(51) Int. Cl.
*B29D 22/02* (2006.01)
*A61M 25/10* (2013.01)
*A63H 27/10* (2006.01)
*A61M 29/02* (2006.01)

(52) U.S. Cl.
CPC ..... *A63H 27/10* (2013.01); *A61M 29/02* (2013.01); *A63H 2027/1041* (2013.01); *Y10T 29/49826* (2015.01); *Y10T 428/13* (2015.01); *Y10T 428/1334* (2015.01)

(58) Field of Classification Search
CPC ..... A63H 27/10; A63H 2027/1041; Y10T 29/49826; Y10T 428/1334; A61M 29/02
USPC ..... 446/220; 604/347, 349, 101.02; 428/34.1, 35.2; 600/38; 128/845
See application file for complete search history.

(56) References Cited

U.S. PATENT DOCUMENTS

| | | | | |
|---|---|---|---|---|
| 4,911,674 | A | 3/1990 | Cole | |
| 5,295,892 | A | 3/1994 | Felton | |
| 5,306,194 | A * | 4/1994 | Epstein | 446/224 |
| 5,458,559 | A | 10/1995 | Gauntlett | |
| 5,819,448 | A | 10/1998 | Kieves et al. | |
| 6,318,013 | B1 * | 11/2001 | Cope | 40/736 |
| 6,736,841 | B2 | 5/2004 | Musbach et al. | |
| 8,349,417 | B2 * | 1/2013 | Heffernan | 428/35.2 |
| 8,663,087 | B2 * | 3/2014 | Kolar | 600/38 |
| 2005/0015047 | A1 * | 1/2005 | Shah | 604/101.02 |
| 2006/0264856 | A1 * | 11/2006 | Wong | 604/349 |
| 2007/0167973 | A1 | 7/2007 | Stupecky et al. | |
| 2008/0172079 | A1 | 7/2008 | Birk | |

FOREIGN PATENT DOCUMENTS

| | | |
|---|---|---|
| WO | 93/17768 A1 | 9/1993 |
| WO | 9317768 | 9/1993 |

* cited by examiner

*Primary Examiner* — Carlos Lopez
(74) *Attorney, Agent, or Firm* — Perkins Coie LLP

(57) ABSTRACT

A self sealing inflatable article including an inflatable body portion and a neck portion having an opening, a ring member supporting the opening of the article and a plug member for sealing the opening wherein at least a portion of the body portion of the article is invaginated through the opening of the article with the plug member associated with the invaginated portion.

13 Claims, 7 Drawing Sheets

SELF-SEALING INFLATABLE ARTICLE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED APPLICATIONS

This application is [an] *a reissue of U.S. Patent No. 8,349,417 issued Jan. 8, 2013 which is a* U.S. national phase application under 35 U.S.C. §371 based upon co-pending International Application No. PCT/US2008/001725 filed on Nov. 21, 2008[. Additionally, this U.S. national phase application] *and additionally* claims the benefit of priority of co-pending International Application No. PCT/AU2008/001725 filed on Nov. 21, 2008, and Australian Application Nos. 2007906391 filed on Nov. 22, 2007 and 2008900021 filed on Jan. 3, 2008. The entire disclosures of the prior applications are incorporated herein by reference. The international application was published on May 28, 2009 under Publication No. WO 2009/065177 A1.

FIELD OF THE INVENTION

The present invention relates to inflatable articles such as balloons and similar and particularly to articles which are self sealing upon inflation.

BACKGROUND ART

A balloon is a flexible bag normally filled with a gas, such as helium, hydrogen or air. Some balloons are purely decorative, others are used for specific purposes. Early balloons were made of dried animal bladders. Modern balloons can be made from materials such as rubber, latex, chloroprene or a nylon fabric.

Balloons have a number of uses including for flight, in entertainment or as decoration and medical uses as well, for example, large balloons filled with hot air or buoyant gas have been used as flying machines since the 18th century.

Party balloons are mostly made of natural latex tapped from rubber trees and can be filled with air, helium, water, or any other suitable liquid or gas. The rubber allows for elasticity which makes the volume adjustable. Most of this rubber is made from recycled material, such as used vehicle tyres.

Filling with air is performed with the mouth, with a manual or electric inflator (such as a hand pump) or a source of compressed air.

Angioplasty is a surgical procedure in which very small balloons are inserted into blocked or partially blocked blood vessels near the heart. Once in place, the balloon can be inflated to clear or compress arterial plaque, and to stretch the walls of the vein. A small stent can be inserted in its place to keep the vessel open after the balloon's removal.

Certain catheters have balloons at their tip to keep them from slipping out, for example, the balloon of a Foley catheter is inflated when the catheter is inserted into the urinary bladder and to secure its position.

Regardless of their application, there have been many attempts in the art to provide a balloon or other inflatable article with self sealing action or characteristics. One example of an attempt to provide a self sealing toy balloon is taught in U.S. Pat. No. 2,625,770 which includes a pair of balloons, one located inside the other with the necks joined in a sealed relationship and with small passageways in the inner balloon for the escape of air therefrom into the outer balloon.

An example of a self sealing balloon for medical use is taught in U.S. Pat. No. 6,736,793. The balloon has an elastomeric membrane and a proximal opening with a self-sealing valve made up of a valve body for receiving an inflation instrument to inflate the balloon. The valve body is preferably formed of a biocompatible elastomeric material and includes a base portion and a sealing portion. The base portion is bonded to the elastomeric membrane so as to seal the proximal opening of the balloon. The sealing portion is located within the balloon and extends distally from the base into the balloon. The sealing portion is compressibly sealable in response to a pressure within the balloon following inflation of the balloon and removal of the inflation instrument.

There are also many examples of balloons or other inflatable articles that are provided with elaborate and complex valve arrangements which are positioned in the inlet of the balloon or other inflatable article during an assembly step either before use or during manufacture.

It will be clearly understood that, if a prior art publication is referred to herein, this reference does not constitute an admission that the publication forms part of the common general knowledge in the art in Australia or in any other country.

SUMMARY OF THE INVENTION

The present invention is directed to a self sealing inflatable article, which may at least partially overcome at least one of the above-mentioned disadvantages or provide the consumer with a useful or commercial choice.

In one form, the invention resides in a self sealing inflatable article including an inflatable body portion and a neck portion having an opening, a ring member supporting the opening of the article and a plug member for sealing the opening wherein at least a portion of the body portion of the article is invaginated through the opening of the article with the plug member associated with the invaginated portion.

In a second form, the invention resides in a method for manufacturing a self-sealing inflatable article including the steps of a) Providing an inflatable body portion and a neck portion having an opening, a ring member supporting the opening of the article and a plug member for sealing the opening;

b) Invaginating at least a portion of the body portion of the article through the opening with the plug portion associated with the invaginated portion; and c) Inflating the article by inserting an inflating fluid into a cavity defined between the body portion and the invaginated portion.

The inflatable article of the present invention is particularly directed towards a self sealing balloon for various uses including use in the entertainment and medical fields. However, it is also anticipated that depending upon the shape in which the article is made, it may have other uses such as for example, an artificial orifice finding application as a sex aid.

The article will be described with reference particularly to its application as a balloon unless otherwise stated.

Balloons (and the inflatable article of the present invention) will typically be manufactured from a liquid rubber material, the most common form of which is latex, but depending upon the application, materials such as silicone may be used. The article may be coloured or patterned. Balloons are normally coloured using a pigment that is added to the latex. The pigments may be either organic or inorganic compounds and typically result in the article absorbing certain wavelengths of visible light and reflecting others.

The strength of the preferred material used (latex) can be affected by the pigment if the pigment particle is large in size and interferes with the film continuity and if the pigment reacts with any of the other ingredients in the latex. Preferably, where the article is coloured such as in balloons, the pigments used are water dispersions of very small particle size, which decreases the interactions with other ingredients in the latex.

The natural rubber latex that is most commonly used comes from the sap of the rubber tree.

The methodology of manufacturing an inflatable article such as the present invention is perhaps most easily described with reference to balloon manufacturing. To make the rubber tree sap suitable for balloon production, curing agents, accelerators, oil, colour, and water are typically added. After these are added, the latex composition, typically in a liquid form, is put in an open top tank, and the balloon form, which is in the shape of a balloon, is dipped into the latex composition.

Before the form is dipped into latex, it is dipped into a coagulant that causes the rubber particles of the latex to collect on the form. The coagulant material is typically calcium nitrate, water, and/or alcohol. After the coagulant-coated form is dried, it is then dipped into the compounded latex. Then the latex coated form passes through a set of revolving brushes that rolls the balloon neck into the bead that is used to aid in the inflation of the balloon. The latex-coated form is then washed in hot water to remove any unused nitrate (the leaching step). Following the leaching, the form is put in an oven to cure. The most preferred parameters for the oven is at a temperature of between approximately 90 to 110 for about 20-25 minutes. When cured, the rubber balloon is removed from the form (stripped).

The form used according to the present invention will be shaped differently according to the application to which the formed article is to be put.

Each balloon form is the shape and size of the uninflated balloon. For example, a balloon form for a round balloon is shaped like an inverted light bulb. The forms are arranged into rows and dipped into liquid latex in assembly line fashion. The latex at the top (thin) end of the form becomes the "lip" when it is rolled down (toward the wide end) by a device which looks like a small motorized brush. As the rows of forms progress down the line, they pass between rotating, cone shaped brushes that are positioned horizontally, one on each side of each row of forms, pointing at the approaching forms. The brushes turn in opposite directions and are positioned so they touch the forms on each side. The point of the brushes start rolling the lip, and the lips continues to form as the row of forms moves along the line from the point to the larger end of the brushes. This occurs while the latex is still uncured, just before it is vulcanized.

The form for balloons may alternatively be elongate, spherical or shapeless. It is noted at this juncture that the formed article will normally be easier to inflate if the article is more elongate. Shorter, wider articles are not only more difficult to invaginate, but are also generally more difficult to inflate.

Another particularly preferred shape has an elongate neck portion and a body portion having a bulbous main portion and an elongate tip portion located on the main portion, generally opposite the neck portion. The tip portion will preferably be provided during manufacture of the article and the form will be correspondingly shaped. The provision of the elongate tip portion will be particularly advantageous when the raw article is invaginated with the tip portion usually forming the invaginated portion. This invagination is much simpler to accomplish if the tip portion is elongate and approximately the length of the bulbous main portion and the elongate neck portion.

There is preferably only a single opening provided on the article. The opening is in the neck portion and will typically be at least partially occluded by the tip portion when invaginated and normally totally occluded after inflation of the article.

There may alternatively be more than one opening. For example, the device could be made in a hollow configuration with a hollow tube or similar extending through the invaginated portion, and through the plug portion.

The article may also be formed with one or more layers of material. For higher demand applications such as medical purposes, there may be two or more layers provided, one layer inside another. The layers may be separate from one another or attached together.

The article of the invention also includes a ring member supporting the opening of the article. The ring member may be as simple as the rolled portion of the neck formed during removal of the article from the form during manufacture. In this configuration, the ring portion will normally be flexible.

The ring may alternatively be a ring member provided separately from the neck and body portions. More than one ring member may be provided, particularly where the article is formed from more than one layer. The ring member preferably stabilises the plug member after invagination of the tip portion. The ring member will therefore preferably define a dimensionally stable opening size. If more than one ring member is provided, there will preferably be an outer ring member and an inner ring. The inner ring member may be provided between the neck portion and a folded back portion of the neck member and the outer ring member is preferably provided outside the folded back portion.

The ring may be located on the article before invagination of the tip portion but preferably, the ring will be located after invagination and prior to inflation. The body portion of the article can then be threaded through the ring until the ring member is adjacent the opening of the article. Inflation of the article then forces the ring member upwards on the neck portion but its travel is prevented by the plug member.

More than one ring member may be used. Where more than one ring member is used, the ring members may be shaped to correspond to each other to limit or prevent movement of the rings relative to one another. In particular, a pair of rings may be provided, one of the rings being an annular ring with a width (or thickness) dimension larger than a height dimension (as opposed to a cylindrical ring with a height dimension larger than a width or thickness dimension) which may allow the article to be more easily gripped or held in use.

The second of the pair of rings where provided is preferably shaped to be located within the first ring and to be at least temporarily retained there. The second ring may have a depression or similar into which the first ring may be at least partially received. A portion of the second ring maybe arcuate in order to allow more convenient inflation of the article. There may be some degree of snap-fit between the first and second rings which may also be designated an outer and inner ring respectively.

The plug member is preferably able to be forced through the opening of the article during the invagination process. It may therefore be capable of deformation in order to pass the dimensionally stable opening defined by the ring member. The plug member is normally located on the outside of the tip portion prior to invagination and after invagination, is located adjacent the opening and the ring member.

As stated above, the plug member may be deformable. According to a particularly preferred embodiment, the plug member is deformable prior to and during invagination so as to pass the ring member, but is non-deformable after invagination in order to hold its shape and prevent the pressure exerted during and after inflation from drawing or forcing the plug member back through the opening.

Any method or means can be provided to accomplish this transition, but normally the plug member will be formed of a settable or curable material. It could also be formed of a deployable mechanism. It is particularly preferred that the plug member is formed of resinous settable material or system. For example, a two part polymerisation system may be provided in different beads or other containers small enough to pass the opening and ring member with little resistance. After passing the ring member and opening, the beads or containers may be ruptured allowing the two parts of the system to react to form a settable material for the plug member.

Many settable polymer systems are thermosetting. That is, they require heat to initiate the reaction which "sets" the polymer. Preferably, the amount of heat will be quite small such as may be provided by rubbing the beads in the tip portion together between a user's hands, but high enough that the reaction is not initiated by latent heat during transport or similar. The stability of the two part system may be particularly important and is better controlled by providing rupturable beads containing each of the two parts. In this manner, the reaction cannot be initiated until the beads are ruptured, regardless of how much heat is applied.

The settable system will usually involve cross-linking of the polymer chains as opposed to linear polymerisation.

The plug member may also be manufactured of material having good deformability in a first direction and limited deformability in a second direction. These materials are called unidirectional materials and are normally composite materials. The plug member can then be forced through the opening with the plug deformed in the first direction and once past the opening, the plug member can then be rotated to engage the opening and/or ring member with the plug member oriented in the second direction. Other methods include dielectric materials which are deformable until an electrical current is passed through them whereupon they become solid, preferably permanently.

Instead of passing the plug member through the ring member, a further alternative method of invaginating the article may be realised by folding the opening outwardly about the body portion and upwardly toward the plug member. In this manner, the plug can be substantially of any form, shape or rigidity as it is not required to pass the ring member.

The plug member will typically be larger in cross-section to prevent re-passing the opening. It is particularly preferred that the plug is conical in shape.

The plug member may also have an elongate portion adapted to be used to attach the plug to the article whilst maintaining the plug portion separate to the interior of the article. In particular, the elongate portion may extend from the plug member and may have a bulbous or enlarged head portion at or adjacent an end. Normally, the elongate and bulbous portion may be forced into part of the wall of the article to deform but not pierce the article and a resilient fastener may be inserted into the interior of the article and over the bulbous portion, clamping the wall to the plug member.

The invagination of a portion of the body of the article typically forms a channel between the neck portion and the invaginated portion allowing for inflation of the article. Inflation expands the inner chamber of the article also formed by the invagination, exerting tension on the article body and neck portions forcing the plug member into the opening to seal the opening. One advantage of this system is that the more the article is inflated, the greater the pressure created in the article and the tighter the seal created.

With regard to inflation, any fluid or semi-fluid may be used to inflate the article. During trialling of the apparatus, air and water were two fluids used which each had the desired inflation.

The article also has a closed orifice formed by the tip portion and the main portion. This orifice may find application as a sex aid amongst other things such as a medical collection vessel. As the orifice is sealed, it is ideal for the temporary storage of fluids. The article itself will typically be small in its uninflated state and therefore be simple and cost effective to store and transport. The small size also lends itself to the storage of the article in dispensing machines or the like.

There are normally a pair of separate cavities created by the invagination of the article and a fluid or material may be held in each cavity without contamination of the material in the other of the cavities. Inserting materials into both may also form the seal of the plug with the neck. In this form, the cavity formed by invagination and normally associated with the plug portion of the article (designated the "head cavity") may be sealed by twisting the neck portion and then allowing the natural bias of the material of construction to seal the neck. The device may be used in this manner as a transport vessel.

According to an alternative embodiment, a self sealing article including a body portion and a neck portion having a neck opening, a body opening in the body portion, a ring member supporting a body opening and a plug member for sealing the neck opening wherein at least a portion of the neck portion of the article is invaginated through the body opening of the article with the plug member sealing against the ring member.

In a fourth form, the invention resides in a method for manufacturing a self-sealing inflatable article including the steps of a) Providing a body portion and a neck portion having a neck opening, a ring member supporting a neck opening and a plug member for sealing the neck opening;
b) Invaginating at least a portion of the body portion through the neck opening with the plug member sealing against the ring member; and
c) Inflating the article by inserting an inflating fluid into a cavity defined between the body portion and the invaginated portion.

The invaginated article may be formed by forcing a portion of the neck portion of the article through the ring member and the body opening. This draws the plug member to the ring member and also forms a containment portion between the invaginated body portion and the neck portion. Inflation of the containment portion by insertion of material into the containment portion exerts force on the body and neck portions sealing the plug member against the ring member.

Normally the body portion and the neck portion will be manufactured of a resilient material.

BRIEF DESCRIPTION OF THE DRAWINGS

Various embodiments of the invention will be described with reference to the following drawings, in which.

DETAILED DESCRIPTION OF THE PREFERRED EMBODIMENT

According to a preferred aspect, a self sealing inflatable article is provided. The self-sealing article is described with particular reference to a balloon but has alternative applications as described previously.

Figure 2:
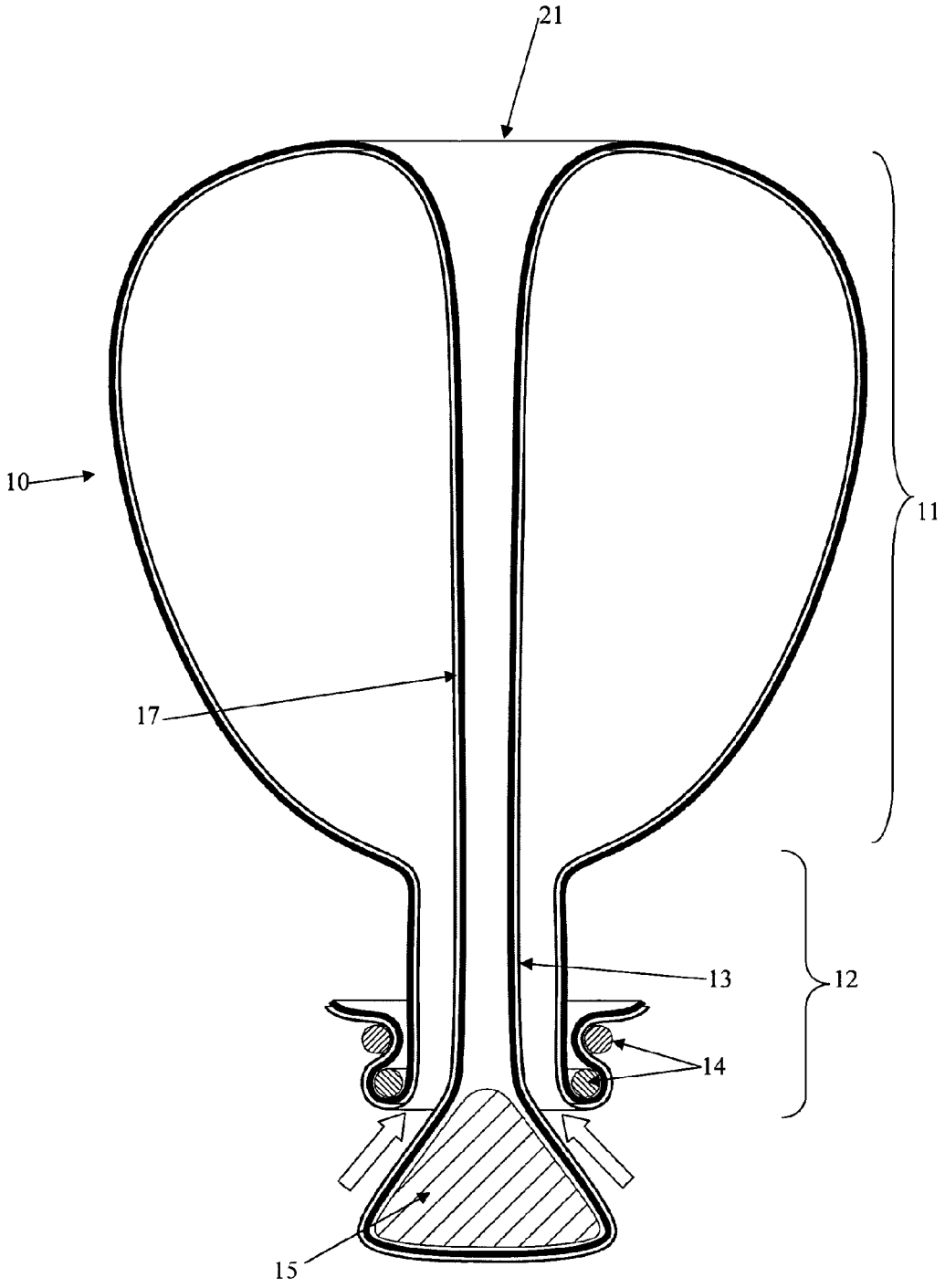
FIG. 2 is a sectional side schematic view of the article illustrated in FIG. 1 after invagination.

The self sealing inflatable article 10 as illustrated in FIG. 2 in particular, includes an inflatable body portion 11 and a neck portion 12 having an opening 13, a ring member 14 supporting the opening 13 of the article 10 and a plug member 15 for sealing the opening 13 wherein at least a portion of the body portion 11 of the article is invaginated through the opening 13 of the article with the plug member 15 associated with the invaginated portion.

The inflatable article of the present invention will typically be manufactured in a manner similar to that of a conventional balloon and from a liquid rubber material, the most common form of which is latex.

To make the rubber tree sap suitable for balloon production, curing agents, accelerators, oil, colour, and water are typically added. After these are added, the latex composition, typically in a liquid form, is put in an open top tank, and the balloon form, which is in the shape of a balloon, is dipped into the latex composition.

Before the form is dipped into latex, it is dipped into a coagulant that causes the rubber particles of the latex to collect on the form. The coagulant material is typically calcium nitrate, water, and/or alcohol. After the coagulant-coated form is dried, it is then dipped into the compounded latex. Then the latex coated form passes through a set of revolving brushes that rolls the balloon neck into the bead that is used to aid in the inflation of the balloon. The latex-coated form is then washed in hot water to remove any unused nitrate (the leaching step). Following the leaching, the form is put in an oven to cure. The most preferred parameters for the oven is at a temperature of between approximately 90 to 110° for about 20-25 minutes. When cured, the rubber balloon is removed from the form (stripped).

The form used according to the present invention will be shaped differently according to the application to which the formed article is to be put. The form for an article of the present invention may alternatively be elongate, spherical or irregularly shaped. It is noted at this juncture that the formed article will normally be easier to inflate, the more elongate the article is. Shorter, wider articles are not only more difficult to invaginate, but are also generally, more difficult to inflate.

Each balloon form is the shape and size of the uninflated balloon. For example, a balloon form for a round balloon is shaped like an inverted light bulb. The forms are arranged into rows and dipped into liquid latex in assembly line fashion. The latex at the top (thin) end of the form becomes the "lip" when it is rolled down (toward the wide end) by a device which looks like a small motorized brush. As the rows of forms progress down the line, they pass between rotating, cone shaped brushes that are positioned horizontally, one on each side of each row of forms, pointing at the approaching forms. The brushes turn in opposite directions and are positioned so they touch the forms on each side. The point of the brushes start rolling the lip, and the lips continues to form as the row of forms moves along the line from the point to the larger end of the brushes. This occurs while the latex is still uncured, just before it is vulcanized.

Figure 1:
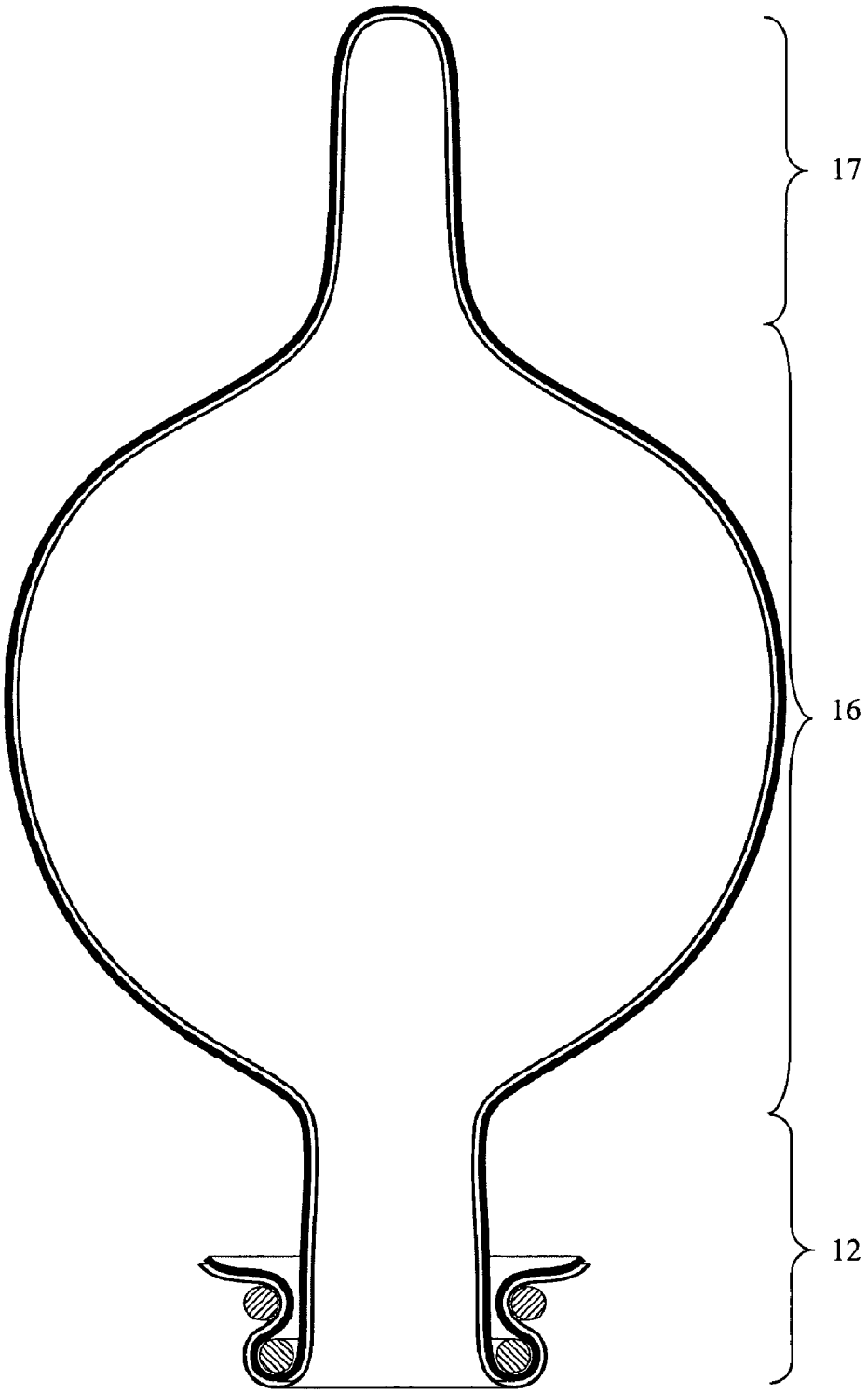
FIG. 1 is a sectional side schematic view of an article according to a preferred embodiment of the present invention prior to invagination.

The article 10 of the illustrated embodiment has an elongate neck portion 12, and a body portion 11 having a bulbous main portion 16 and an elongate tip portion 17 located on the main portion 16, generally opposite the neck portion 12. The tip portion 17 is formed during manufacture of the article and the form is correspondingly shaped. The provision of the elongate tip portion 17 is particularly advantageous when the unassembled article, as illustrated in FIG. 1, is invaginated with the tip portion 17 forming the invaginated portion. This invagination is much simpler to accomplish if the tip portion 17 is elongate and approximately the length of the bulbous main portion 16 and the elongate neck portion 12.

The opening 13 is in the neck portion 12 and is at least partially occluded by the tip portion 17 when invaginated, as can be seen from FIG. 2 and normally totally occluded after inflation of the article 10.

The illustrated article is formed with two layers of material. For higher demand applications such as medical purposes, there may be two or more layers provided, one layer inside another. The layers may be separate from one another or attached together.

Figure 4:
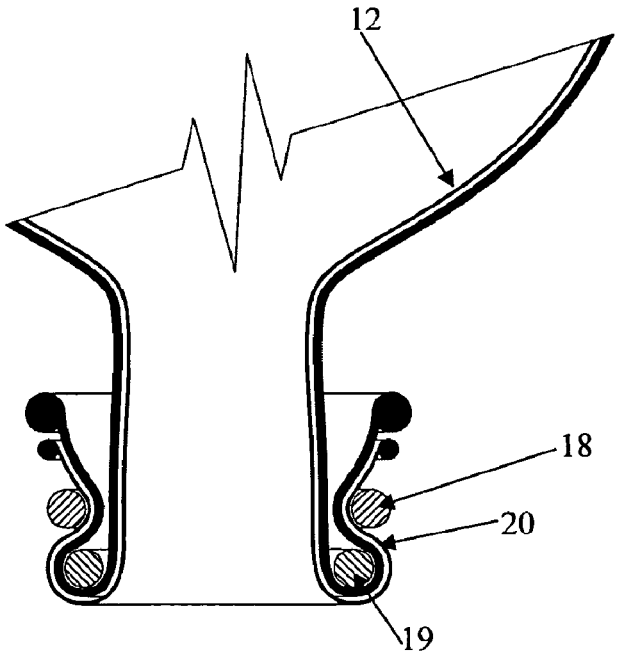
FIG. 4 is a sectional side schematic view of the opening with ring members according to a preferred embodiment of the present invention.

The illustrated article also includes an outer ring member 18 and an inner ring member 19, best illustrated in FIG. 4. The ring members stabilise the plug member 14 after invagination of the tip portion 17. The ring members define a dimensionally stable opening size. The inner ring member 19 is provided between the neck portion 12 and a folded back portion 20 of the neck portion, and the outer ring member 18 is provided outside the folded back portion 20.

The ring members 18, 19 are located after invagination and prior to inflation. The body portion 11 of the article 10 can then be threaded through the ring members 18, 19 until the ring members are adjacent the opening 13 of the article. Inflation of the article then forces the ring members 18, 19 upwards on the neck portion 12 but its travel is prevented by the plug member 15.

The plug member 15 is able to be forced through the opening 13 of the article during the invagination process. It should therefore be capable of deformation in order to pass the dimensionally stable opening defined by the ring member (s). The plug member 15 is normally located on the outside of the tip portion 17 prior to invagination and after invagination, is located adjacent the opening 13 and the ring member(s).

As stated above, the plug member 15 is preferably deformable. According to a particularly preferred embodiment, the plug member 15 is deformable prior to and during invagination so as to pass the ring member, but is non-deformable after invagination in order to hold its shape and prevent the pressure exerted during and after inflation from drawing or forcing the plug member 15 back through the opening 13.

Any method or means can be provided to accomplish this transition, but normally the plug member will be formed of a settable or curable material, and according to the preferred embodiment, of a two part polymerisation system provided in different beads or other containers small enough to pass the opening 13 and ring member(s) with little resistance. After passing the ring member(s) and opening 13, the beads or containers are ruptured allowing the two parts of the system to react to form a settable material for the plug member.

Figure 3:
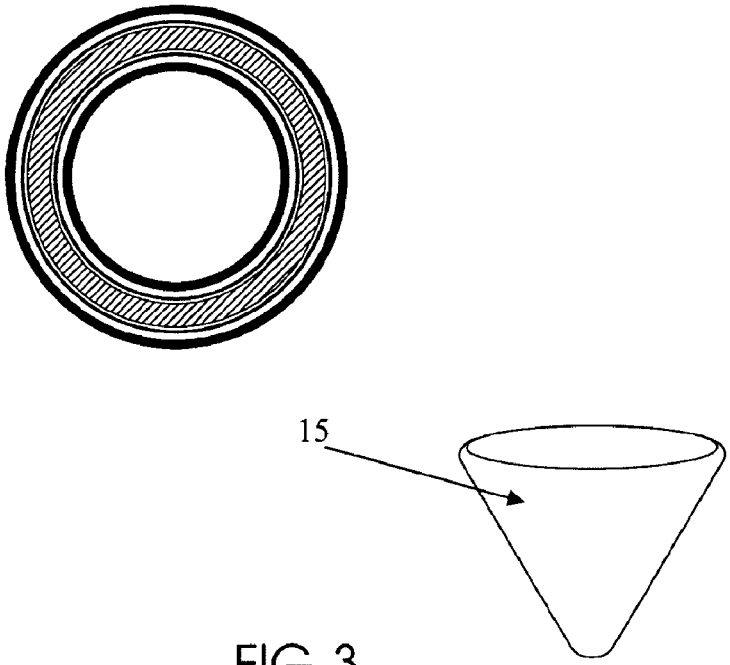
FIG. 3 is a sectional top schematic and perspective view of a preferred embodiment of plug member according to the present invention.

The plug member 15 is larger in cross-section than the opening 13 to prevent re-passing the opening 13. It is particularly preferred that the plug is conical in shape as illustrated in FIG. 3.

The preferred method for manufacturing a self-sealing inflatable article includes the steps of providing an inflatable body portion and a neck portion having an opening, a ring member supporting the opening of the article and a plug member for sealing the opening, invaginating at least a portion of the body portion of the article through the opening with the plug portion associated with the invaginated portion; and inflating the article by inserting an inflating fluid into a cavity defined between the body portion and the invaginated portion as illustrated by the arrows in FIG. 2.

The invagination of a portion of the body of the article forms a channel between the neck portion 12 and the invaginated portion allowing for inflation of the article. Inflation expands the inner chamber of the body portion 11 also formed by the invagination, exerting tension on the article body and neck portions 12 forcing the plug member 15 into the opening 13 to seal the opening 13. One advantage of this system is that the more the article is inflated, the greater the pressure created in the article and the tighter the seal created.

With regard to inflation, any fluid or semi-fluid may be used to inflate the article. During trialling of the apparatus, air and water were two fluids used which each had the desired inflation.

The article also has a closed orifice 21 formed by the tip portion 17, the main portion 16 and the plug member 15. This orifice 21 may find application as a sex aid amongst other things such as a medical collection vessel. As the orifice 21 is sealed, it is ideal for the temporary storage of fluids.

The article 10 itself will typically be small in its uninflated state and therefore be simple and cost effective to store and transport. The small size also lends itself to the storage of the article in dispensing machines or the like.

Figure 5:
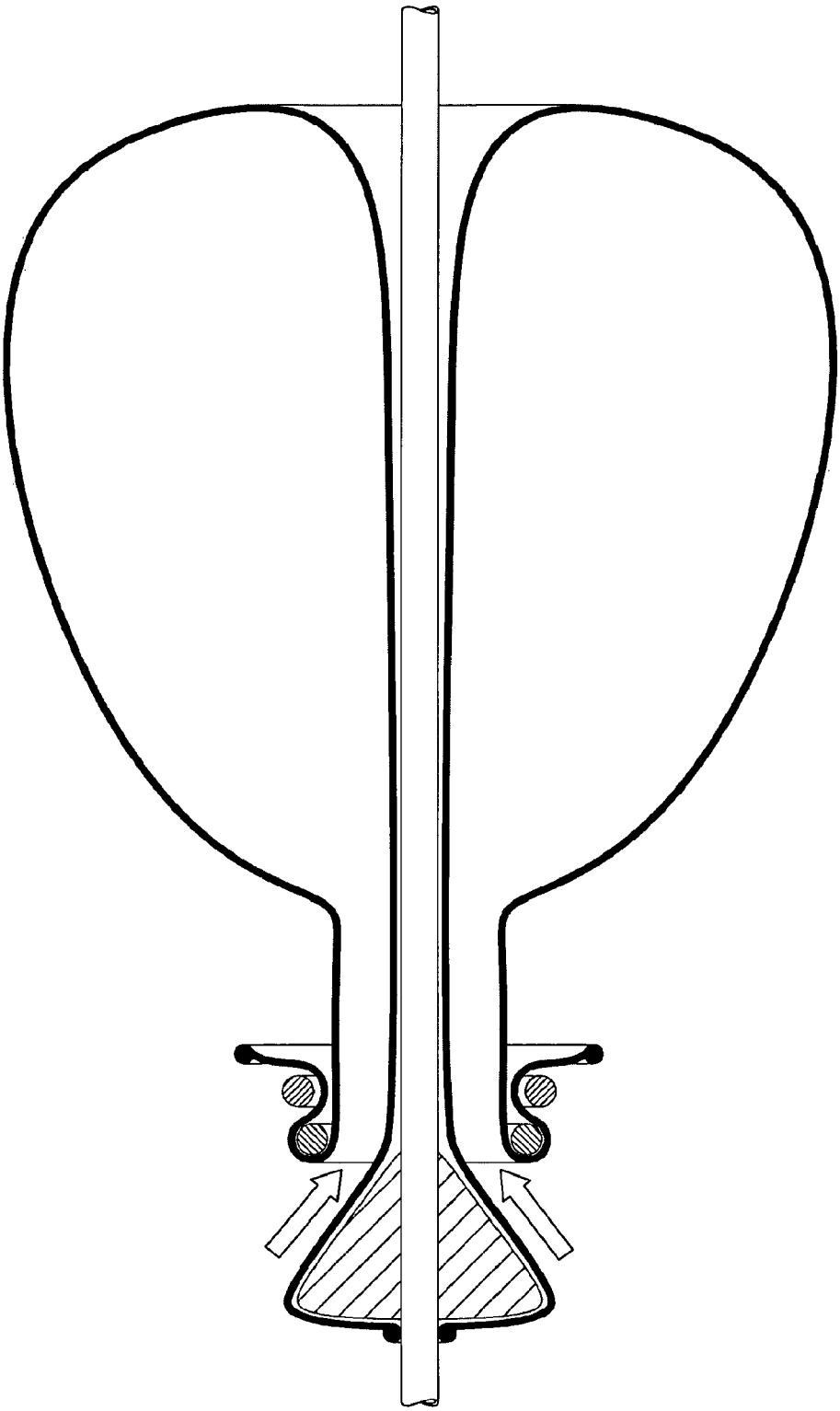
FIG. 5 is a sectional side schematic view of an alternative hollow configuration of the device of the present invention.

As illustrated in FIG. 5, more than one ring can be used, as in FIGS. 1, 2 and 4, but in alternative configurations. The inner 19 and outer 18 ring members illustrated in FIG. 5 are shaped to correspond to each other to limit or prevent movement of the rings relative to one another. According to the embodiment in FIG. 5, the outer ring is an annular ring with a width (or thickness) dimension larger than a height dimension which may allows the article to be more easily gripped or held in use, utilising the outer ring 18.

The inner ring 19 is shaped to be located within the outer ring 18 and to be at least temporarily retained there. The inner ring 19 has a depression 22 into which the outer ring 1 is at least partially received. An outer portion of the inner ring 19 is arcuate in order to allow more convenient inflation of the article.

Figure 6:
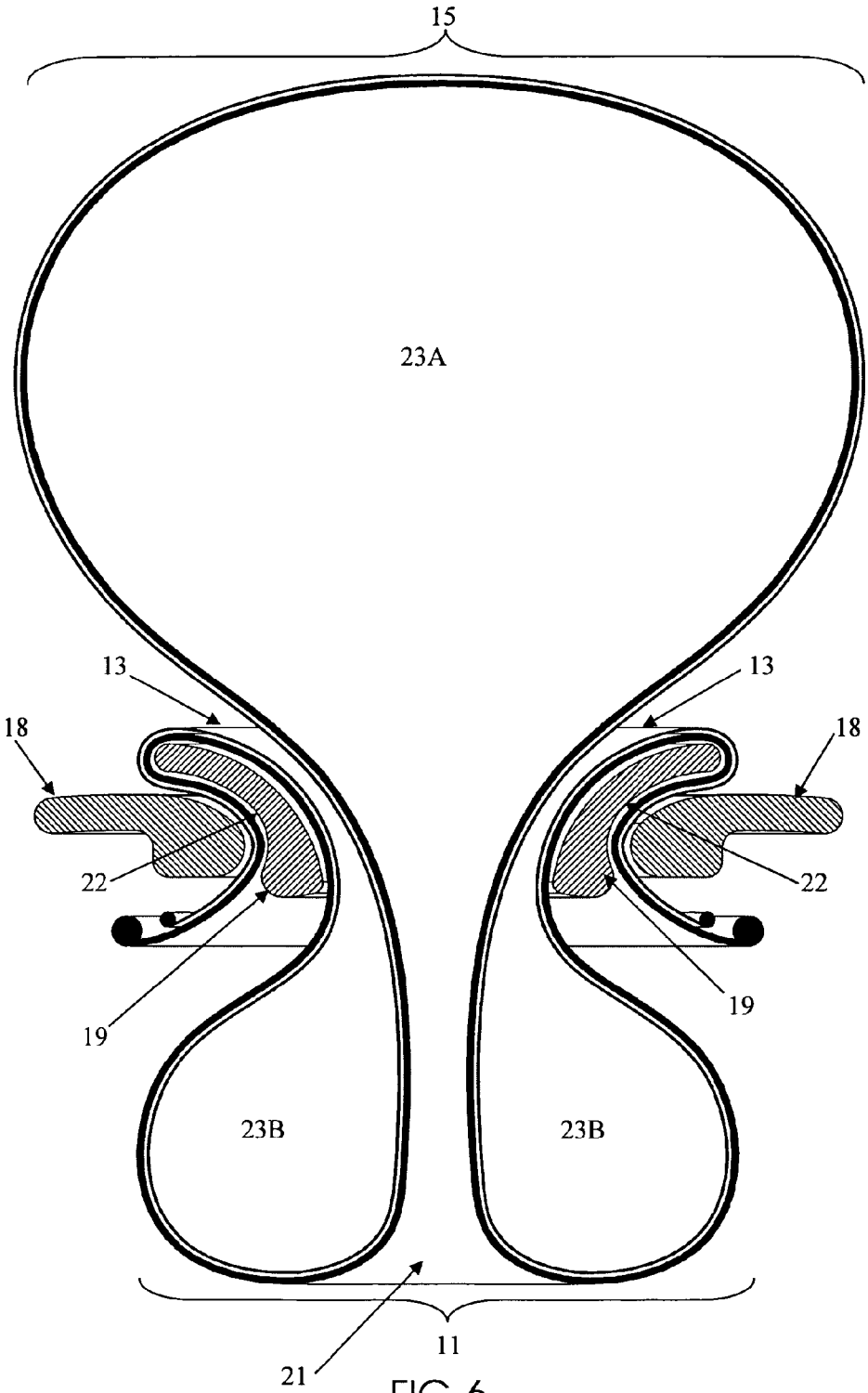
FIG. 6 is a sectional side schematic view of an article according to an alternative embodiment after invagination.
Figure 7:
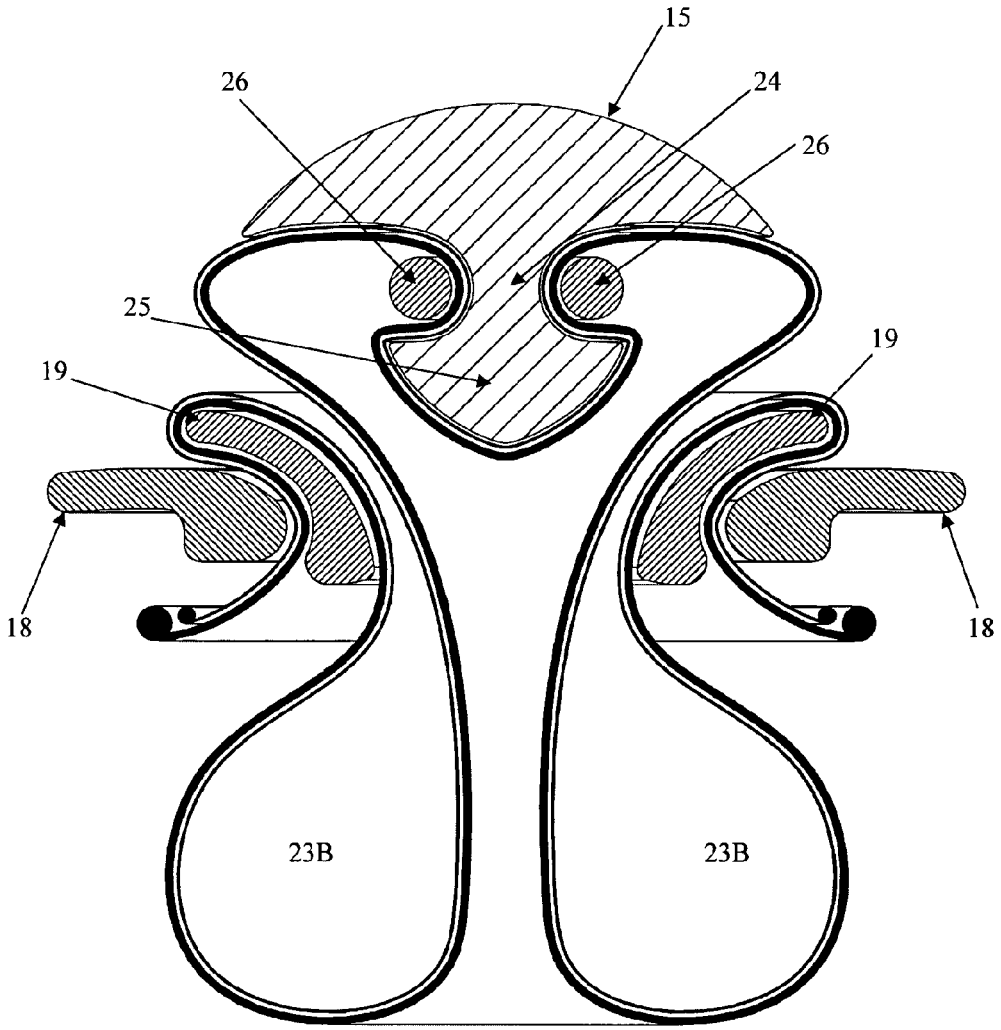
FIG. 7 is a sectional side schematic view of an article according to a further alternative embodiment after invagination.

According to the embodiment illustrated in FIG. 6, there are a pair of separate cavities 23A and 23B created by the invagination of the article and a fluid or material can be held in each cavity without contamination of the material in the other of the cavities. Inserting materials into both may also form the seal of the plug 15 with the neck without the provision of the plug as a separate component as illustrated in FIGS. 2 and 7 in particular. In this form, the cavity 23A formed by invagination and normally associated with the plug portion of the article (designated the "head cavity") can be sealed by twisting the neck portion and then allowing the natural bias of the material of construction to seal the neck 12.

As illustrated in FIG. 7, the plug 15 can also have an elongate portion 24 adapted to be used to attach the plug 15 to the article whilst maintaining the plug 15 separate to the interior of the article. In particular, the elongate portion 24 extends from the plug 15 and has a bulbous or enlarged head portion 25 at or adjacent an end. Normally, the elongate portion 24 and bulbous portion 25 are forced into part of the wall of the article to deform but not pierce the article and a resilient band 26 is inserted into the interior of the article and over the bulbous portion 25, clamping the wall to the plug 15.

Figure 8:
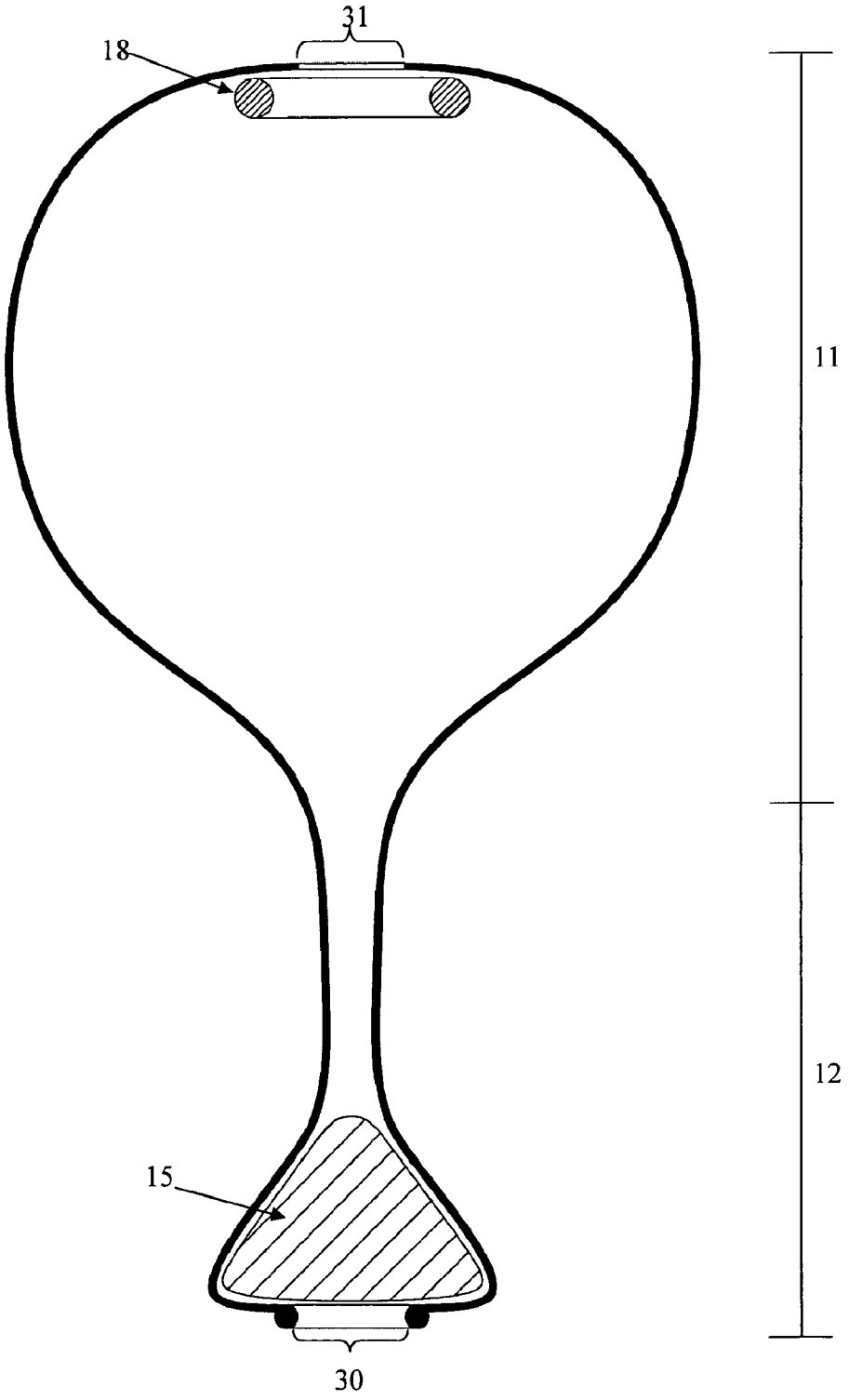
FIG. 8 is a sectional side schematic view of an article according to still a further embodiment of the invention prior to invagination.

According to an alternative embodiment illustrated in FIG. 8, the self sealing article includes a body portion 11 and a neck portion 12 having a neck opening 30, a body opening 31 in the body portion 11, a ring member 18 supporting the body opening 31 and a plug member 15 for sealing the neck opening 30 wherein at least a portion of the neck portion 12 is invaginated through the body opening 31 with the plug member 15 sealing against the ring member 18.

Manufacturing the self-sealing inflatable article of this embodiment includes the steps of a) Providing a body portion and a neck portion having a neck opening, a ring member supporting a body opening and a plug member for sealing the neck opening;

b) Invaginating at least a portion of the neck portion through the body opening with the plug member sealing against the ring member; and c) Inflating the article by inserting an inflating fluid into a cavity defined between the body portion and the invaginated portion.

Prior to invagination, the ring member is inserted into the body portion, normally of a balloon or a similar device and the neck opening is then sealed. The body opening can be formed either before or after this step. Once the ring member is properly located supporting the body opening, a portion of the neck portion of the article can then forced through the body opening, by invagination.

This draws the plug member to the ring member and also forms a containment portion between the invaginated body portion and the neck portion. Inflation of the containment portion by insertion of material into the containment portion exerts force on the body and neck portions sealing the plug member against the ring member.

In the present specification and claims (if any), the word "comprising" and its derivatives including "comprises" and "comprise" include each of the stated integers but does not exclude the inclusion of one or more further integers.

Reference throughout this specification to "one embodiment" or "an embodiment" means that a particular feature, structure, or characteristic described in connection with the embodiment is included in at least one embodiment of the present invention. Thus, the appearance of the phrases "in one embodiment" or "in an embodiment" in various places throughout this specification are not necessarily all referring to the same embodiment. Furthermore, the particular features, structures, or characteristics may be combined in any suitable manner in one or more combinations.

The invention claimed is:

1. [A self sealing] *An* inflatable article comprising:

an inflatable body portion[;

a neck portion having an opening;] *having a first opening at a first end, the first opening leading to an elongated passage, said inflatable body portion including* at least [a pair of] *one flexible* ring [members supporting the opening] *at a second end* of the article, wherein the [pair of] *at least one flexible* ring [members comprises an outer ring member and an inner ring member adjacent the outer ring member, the inner ring member is provided between the neck portion and a folded back portion of the neck portion, and the outer ring member is provided outside the folded back portion, wherein the folded back portion is a section of the neck portion that is folded back over itself;] *is formed from an elastic material,* and

*an expandable cavity, a portion of which is formed by said elongated passage, said inflatable body portion, including said elongated passage, being formed from the elastic material; and*

*a neck portion adjacent to the inflatable body portion, the neck portion including* a plug member [for sealing the opening] *at a second end of the elongated passage wherein the second end is substantially opposite the first end and wherein said plug member forms a seal against the at least one flexible ring to define a second opening into the expandable cavity between the plug member and the at least one flexible ring*; *and* wherein [at least a portion of the body portion of the article is invaginated through the opening of the neck portion of the article with the plug member associated with the invaginated portion] *to inflate the article the seal formed between the plug member and the at least one flexible ring is broken and fluid is inserted through the second opening into the expandable cavity*.

2. The [self sealing] inflatable article as claimed in claim 1, wherein the [neck portion has an elongate neck portion, and the body portion having a bulbous main portion and an elongate tip portion located on the main portion, opposite the neck portion] *elastic material is a silicon-based material*.

[3. The self sealing inflatable article as claimed in claim 2, wherein the elongate tip portion has a length approximately a length of the bulbous main portion and the elongate neck portion.]

4. The [self sealing] inflatable article as claimed in claim 1, wherein the *second* opening is [a single opening provided on the article at least partially occluded by the invaginated portion when invaginated and] totally occluded after inflation of the article.

[5. The self sealing inflatable article as claimed in any one of the preceding claims, wherein the article is formed from more than one layer of material for higher demand applications.]

[6. The self sealing inflatable article as claimed in claim 5, wherein the layers are attached together.]

[7. The self sealing inflatable article as claimed in claim 1, wherein the ring member is dimensionally stable against accidental passage of the plug.]

8. The [self sealing] inflatable article as claimed in claim 1, wherein the *at least one flexible* ring [member] is formed integrally with the [neck] *inflatable body* portion.

[9. The self sealing inflatable article as claimed in claim 1, wherein the ring member is separate from the neck and body portions.]

*10. The inflatable article of claim 1 wherein the plug is deformable.*

*11. The inflatable article of claim 10 wherein the body portion has a third opening formed within the plug which leads to a hollow tube which extends through the plug into the elongated passage.*

*12. The inflatable article of claim 1 further comprising a fastener for clamping said plug.*

*13. The inflatable article of claim 1 wherein the article is self sealing.*

*14. The inflatable article of claim 1 wherein the plug is conical shaped.*

*15. The inflatable article of claim 8 wherein the at least one ring is formed of a rolled end portion of said inflatable body portion.*

*16. The inflatable article of claim 1 wherein the fluid is water.*

*17. The inflatable article of claim 1 wherein the article adopts an uninvaginated configuration wherein the seal between the at least one flexible ring and the plug member is fully broken.*

*18. The inflatable article of claim 1 wherein the article is configured for use as a sex aid.*

* * * * *

UNITED STATES PATENT AND TRADEMARK OFFICE

CERTIFICATE OF CORRECTION

PATENT NO. : RE45,963 E
APPLICATION NO. : 13/735624
DATED : September 29, 2015
INVENTOR(S) : Masaya Minamide It is certified that error appears in the above-identified patent and that said Letters Patent is hereby corrected as shown below:

On the Title page, in the Abstract (57):

At line number 5, the words "a [reversing-time segmenting number] *number of consecutive occurrences of reversing motions*" should read -- a *number of consecutive occurrences of reversing motions* [reversing-time segmenting number] --.

At line number 15, the words "of the [reversing-time segmenting number] *number of consecutive occurrences of reversing motions*" should read -- of the *number of consecutive occurrences of reversing motions* [reversing-time segmenting number] --.

At line number 19, the words "to the [reversing-time segmenting number] *number of consecutive occurrences of reversing motions*" should read -- to the *number of consecutive occurrences of reversing motions* [reversing-time segmenting number] --.

In the Specification:

At column 4, line number 12, the words "value of the [reversing-time segmenting number] *number of consecutive occurrences of reversing motions*" should read -- value of the *number of consecutive occurrences of reversing motions* [reversing-time segmenting number] --.

Signed and Sealed this
Twenty-ninth Day of March, 2016

Michelle K. Lee

Michelle K. Lee
*Director of the United States Patent and Trademark Office*

At column 4, line number 23, the words "according to the [reversing-time segmenting number] *number of consecutive occurrences of reversing motions*" should read -- according to the *number of consecutive occurrences of reversing motions* [reversing-time segmenting number] --.

At column 5, line number 2, "a [reversing-time segmenting number] *number of consecutive occurrences of reversing motions*" should read -- a *number of consecutive occurrences of reversing motion* [reversing-time segmenting number] --.

At column 5, line number 11, "to the [reversing-time segmenting number] *number of consecutive occurrences of reversing motions*" should read -- to the number of consecutive occurrences of reversing motions [reversing-time segmenting number] --.

At column 5, line number 13, "The [reversing-time segmenting number] *number of consecutive occurrences of reversing motions*" should read -- The *number of consecutive occurrences of reversing motions* [reversing-time segmenting number] --.

At column 5, line number 19, "the [reversing-time segmenting number] *number of consecutive occurrences of reversing motions*" should read -- the *number of consecutive occurrences of reversing motions* [reversing-time segmenting number] --.

At column 5, line number 21, "denoting the [reversing-time segmenting number, which is a coefficient indicating a number of segments per unit time during a reversing motion] *number of consecutive occurrences of reversing motions.*" should read -- denoting the *number of consecutive occurrences of reversing motions* [reversing-time segmenting number, which is a coefficient indicating a number of segments per unit time during a reversing motion]. --.

At column 5, line number 26, "the [reversing-time segmenting number] *number of consecutive occurrences of reversing motions*" should read -- the *number of consecutive occurrences of reversing motions* [reversing-time segmenting number] --.

At column 5, line number 28, "value of the [reversing-time segmenting number] *number of consecutive occurrences of reversing motions* N" should read -- value of the number *of consecutive occurrences of reversing motions* [reversing-time segmenting number] N. --.

At column 5, line number 30, "Then the [reversing-time segmenting number] *number of consecutive occurrences of reversing motions*" should read -- Then the *number of consecutive occurrences if reversing motions* [reversing-time segmenting number] --.

At column 5, line number 32, "sends the [reversing-time segmenting number] *number of consecutive occurrences of reversing motions* N" should read -- sends the *number of consecutive occurrences of reversing motions* [reversing-time segmenting number] N --.

At column 5, line number 37, "to the [reversing-time segmenting number] *number of consecutive occurrences of reversing motions* N" should read -- to the *number of consecutive occurrences of reversing motions* [reversing-time segmenting number] N --.

At column 5, line number 53, "and the [reversing-time segmenting number] *number of consecutive occurrences of reversing motions* (N)" should read -- and the *number of consecutive occurrences of reversing motions* [reversing-time segmenting number] (N). --.

At column 6, line number 1, "N: [reversing-time segmenting number] the *number of consecutive occurrences of reversing motions*" should read -- N: the *number of consecutive occurrences of reversing motions* [reversing-time segmenting number] --.

At column 6, line number 4, "performed by the [reversing-time segmenting number] *number of consecutive occurrences of reversing motions*" should read -- performed by the *number of consecutive occurrences of reversing motions* [reversing-time segmenting number] --.

At column 6, line number 7, "the [reversing-time segmenting number] *number of consecutive occurrences of reversing motions*" should read -- the *number of consecutive occurrences of reversing motions* [reversing-time segmenting number] --.

At column 6, line number 13, "the [reversing-time segmenting number] *number of consecutive occurrences of reversing motions*" should read -- the *number of consecutive occurrences of reversing motions* [reversing-time segmenting number] --.

At column 6, line number 18, "the [reversing-time segmenting number] *number of consecutive occurrences of reversing motions*" should read -- the *number of consecutive occurrences of reversing motions* [reversing-time segmenting number] --.

At column 6, line number 53, "[reversing-time segmenting number] *number of consecutive occurrences of reversing motions*" should read -- *number of consecutive occurrences of reversing motions* [reversing-time segmenting number] --.

In the Claims:

At column 7, line number 7, claim 1, the words "a [reversing-time segmenting number] *number of consecutive occurrences of reversing motions*" should read -- a *number of consecutive occurrences of reversing motions* [reversing-time segmenting number] --.

At column 7, line number 18, claim 1, the words "of the [reversing-time segmenting number] *number of consecutive occurrences of reversing motions*" should read -- of the *number of consecutive occurrences of reversing motions* [reversing-time segmenting number] --.

At column 7, line number 22, claim 1, the words "to the [reversing-time segmenting number] *number of consecutive occurrences of reversing motions*" should read -- to the *number of consecutive occurrences of reversing motions* [reversing-time segmenting number] --.